United States Patent [19]

Lademann et al.

[11] 3,966,832
[45] June 29, 1976

[54] CONTINUOUS PROCESS FOR PREPARING DERIVATIVES OF BENZENE WITH FLUORINATED SIDE CHAINS FROM THE CORRESPONDING CHLORINE COMPOUNDS

[75] Inventors: Rudolf Lademann, Kelkheim, Taunus; Helmut Lindner, Hofheim, Taunus; Thomas Martini, Neuenhain, Taunus; Peter Paul Rammelt, Hofheim, Taunus, all of Germany

[73] Assignee: Hoechst Aktiengesellschaft, Frankfurt am Main, Germany

[22] Filed: Nov. 7, 1974

[21] Appl. No.: 521,894

[30] Foreign Application Priority Data
Nov. 10, 1973  Germany............................ 2356257

[52] U.S. Cl............................................. 260/651 F
[51] Int. Cl.².................... C07C 25/14; C07C 17/20
[58] Field of Search.................................. 260/651 F

[56] References Cited
UNITED STATES PATENTS 1,967,244   7/1934   Holt et al. ...................... 260/651 F
2,562,159   7/1951   Wojcik et al. .................... 260/651 F FOREIGN PATENTS OR APPLICATIONS
395,227   7/1933   United Kingdom ............. 260/651 F

*Primary Examiner*—D. Horwitz
*Attorney, Agent, or Firm*—Curtis, Morris & Safford

[57] ABSTRACT

Preparation of derivatives of benzene containing $CF_3$ groups from the corresponding compounds containing $CCl_3$ groups (e.g. trichloromethyl benzene) is carried out continuously with excellent yield rates by reaction with liquid hydrogen fluoride in an autoclave above 80°C, (which latter exceeds the stoichiometric proportion by at least 25 mole %). The reactants are fed continuously into the autoclave. The reaction mixture preferably becomes pressurized to at least 20 atmospheres and homogeneous after having reached a certain filling level. The reaction mixture is thereafter withdrawn proportionally to its feeding-in rate. The mixture may be conveyed through one or several additional autoclaves with the final withdrawal of the reaction mixture being out from the terminal autoclave of this cascade. The fluorination products are well known starting and inermediate products for the preparation of dyestuffs and pesticidal compositions.

13 Claims, 1 Drawing Figure

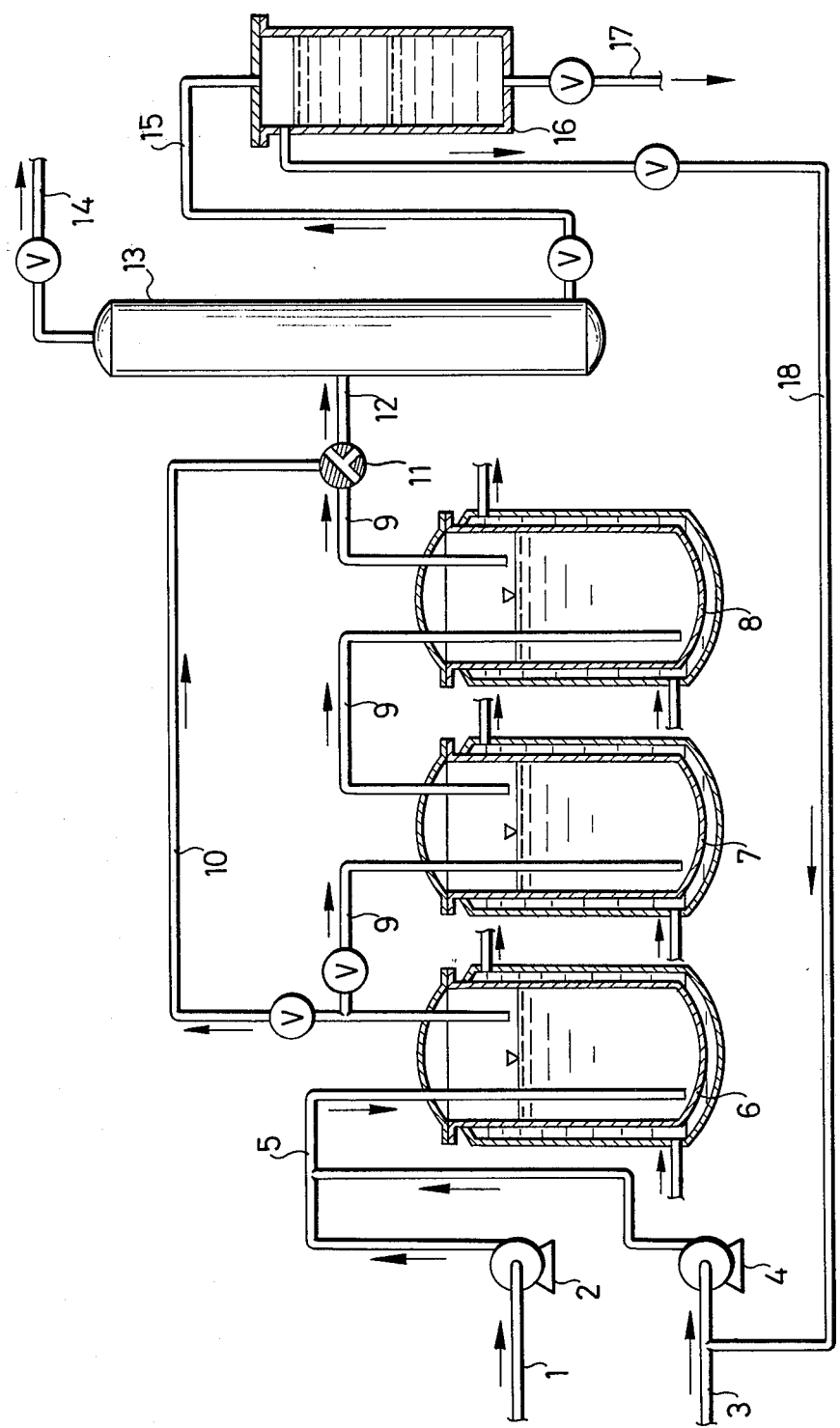

CONTINUOUS PROCESS FOR PREPARING DERIVATIVES OF BENZENE WITH FLUORINATED SIDE CHAINS FROM THE CORRESPONDING CHLORINE COMPOUNDS

Several processes are known for fluorination of chlorine containing substituants linked to the benzene nucleus.

According to U.S. Pat. No. 1,967,244 and to J. Chem. Soc. Suppl. Issue 1 (1949), page 95, trichloromethyl-benzene is fluorinated discontinuously with hydrogen fluoride. German "Auslegeschrift" No. 1,618,390 describes the continuous preparation of derivatives of benzene with one or several trifluoromethyl groups in a flow tube. German "Auslegeschrift" No. 1,543,015 and German "Offenlegungsschrift" No. 2,161,995 describe the fluorination of substituted aromatic substances in the side chain by means of a contact catalyst.

However, all these processes have fundamental drawbacks. For one thing, the discontinuous processing method is stigmatized by an unfavorable space/time yield. For another thing the results show relatively poor conversion rates. Furthermore, the starting components, for example benzotrichloride and hydrogen fluoride, are at first present in two layers which can react at the boundary area only. The pressure mounts spontaneously as soon as the reaction starts briskly upon heating. Though the continuous process in the flow tube shows an improved space/time yield, the conversion rates for some products such as o-chloro-benzotrifluoride at a yield of 83 % and m-trifluoromethyl-benzoylfluoride at a yield of 24 % are unsatisfactory. Specifically, due to resinifications forming on the wall surface, which are relatively large as compared to the small diameter of the tube, the latter is easily prone to obstruction. The location of these obstructions cause considerable difficulties and their removal involves complicated operations.

Consequently highly undesirable production breakdowns result. Besides relying on the use of an additional catalyst, the process according to German "Offenlegungsschrift" No. 2,161,995 has the inconvenience of requiring very large quantities of hydrofluoric acid (exceeding theoretical requirements by at least three times). Besides, the hydrogen chloride formed in course of the reaction has to be blown off continuously because of the low reaction pressure; so that a loss of hydrofluoric acid is unavoidable. Since the described conditions of the process do not allow for a homogeneous solution inside the reaction vessel; therefore thorough mixing is possible only by means of continuous agitation. The reaction time is therefore heavily dependent on the number of strokes (i.e. the stirring rate) of the magnetic type agitator used. The fact is a considerable handicap for transposing the process to a technological scale, because the stirring frequencies applied expose the equipment and its surroundings to great stress. Moreover, the process cannot be carried through in continuous manner, for the separation of the reaction product requires the individual phases to be segregated again from each other so as to achieve isolation of the material sought after. Neither could it be expected that this process would be appropriate for reacting compounds such as m-xylene-hexachloride or m-trichloro-methylbenzoylchloride at reasonable rates of throughput and yield since they are rather difficult to fluorinate.

For all these reasons there exists a genuine interest in the art for a practical process for the preparation of derivatives of benzene with fluorinated side chains which is suitable for large-scale technological operation with high yield rates and with no resin formation.

According to German "Auslegeschrift" No. 1,618,390, it is considered impossible to feed simultaneously the reaction components into an autoclave while the reaction products are being evacuated. Said German "Auslegeschrift" also stipulates that the reaction volume be kept small in order to avoid a sudden increase of pressure at the start of the reaction. This stipulation does not favor, in practical operation, the use of one or several large-volume autoclaves in consecutive order. Moreover, the expectation was that in the context of such an arrangement the conversion rates ought to be lower — according to the spectrum of the residence times — than those of a similar average residence time in a flow tube. This would be all the more true since the number of autoclaves used should be kept as small as possible for technological reasons. To cite an example, the probable residence time would be equal to 0.6 in case of a 2-reactor cascade optimum thorough mixing and at a quotient of actual residence time and average residence time being equal to 1; as compared to a flow tube where this probable residence time is close to 1.

An embodiment of the present invention is a process for the continuous preparation of derivatives of benzene containing trifluoromethyl groups by reacting liquid hydrogen fluoride at an elevated temperature and under pressure with the corresponding compounds containing trichloromethyl groups. The process comprises continuously feeding the reaction components, i.e. hydrogen fluoride and a derivative of trichloromethylbenzene, into an autoclave having a reaction temperature of above 80°C. Most conveniently the autoclave is precharged with liquid hydrogen fluoride while maintaining an excess of at least 25 mole % of the hydrogen fluoride (as compared to the stoichiometric proportion). The reaction mixture is homogeneous after having adjusted the reaction pressure. The mixture is withdrawn after reaching a certain filling level by an amount proportional to the reactants fed thereto. This withdrawal of the reaction mixture is either by means of a value control or is by intermediately being transferred into one or several additional autoclave(s) having also a reaction temperature and therefore is finally withdrawn from the terminal autoclave of this cascade.

This reaction mixture is worked up in known manner, most conveniently by distillation under pressure of the hydrogen chloride formed and by separation of the liquid phase which resolves into two phases. The upper and lighter phase of which, consisting essentially of hydrogen fluoride, can be recycled. The lower and heavier phase contains the reaction product which can be submitted to further purification e.g. by washing, drying and distillation. This work-up method is described by German "Auslegeschrift" No. 1,618,390 and is not a subject of the present invention.

The reaction pressure at which the process of the invention is carried out and which is built up by the formation of hydrogen chloride is not of critical importance. However, so as to assure the preparation of a sufficiently homogeneous reaction mixture (for which the reaction pressure acts as solubilizer) this reaction pressure should exceed 20 absolute atmospheres and generally amount to from 30–50 absolute atmospheres. Its upper limit may be set randomly and depends only on the resistance to pressure of the operational equipment. As far as the quantities of hydrogen chloride formed are concerned, the same may either be discharged in the gaseous state into the work-up area by means of a pressure control valve (and in that case, it is convenient to remove the liquid reaction mixture by means of an ascending pipe through another valve which is subject to a filling level control), or both phases — gaseous and liquid — emerge from the equipment through the same valve which may then be subject to pressure control. The filling level depends on the length of the ascending pipe used.

The reaction temperature should be set above 80°C so as to assure a sufficient reaction speed. It generally varies from 85° to 150°C, preferably from 90° to 130°C. Higher temperatures are possible, but they often induce losses due to resinification to certain products. Moreover, such higher temperatures require costlier and more complicated equipment for resisting corrosion and high temperatures. In case of setting up two or more autoclaves thus forming a cascade, the temperature the individual autoclaves are kept at may be identical or differ from each other.

The autoclaves set up should show a proportion in length to diameter of less than 10:1, preferably 5:1 to 1:1 especially 3:1 to 1:1. They may not outnumber 5, preference is given to a number of from 1 to 3.

The molar excess of hydrogen fluoride as compared to the quantity of the trichloromethyl compound applied should be at least 25 mole % above the stoichiometric value, generally the hydrogen fluoride exceeding by from 30 to 300 mole %, preferably from 40 to 200 mole %.

The throughput for the reaction components is adjusted in such a way that the average residence time in the total equipment is from 30 to 300, preferably from 50 to 100 minutes.

By preheating the reactants to the reaction temperature the residence time required may be shifted into the lower range of these intervals.

The illustration explains the process according to the invention. Generally, the process according to the invention is carried out in such a way that in the first autoclave 6 having a reaction temperature, is present either liquid hydrogen fluoride or — as an equivalent — the most homogeneous possible mixture of a derivative of trifluoromethylbenzene, hydrogen fluoride and hydrogen chloride. The latter homogeneous mixture is added at a quantity which guarantees an interior pressure of at least 20 absolute atmospheres, or the minimum pressure of 20 absolute atmospheres is previously attained by charging hydrochloric acid only and additionally feeding into the autoclave 6 the reactants (i.e. the derivative of trichloromethylbenzene through pipe 1 and a pump 2 as well as liquid hydrogen fluoride through pipe 3 and a pump 4) at the proportion and quantity desired through pipe 5 pumped into the autoclave 6. The quantity of the aforesaid precharged liquid phase is of minor importance, since its sole purpose is to speed up the start of the reaction and to thus avoid a pressure eruption. The quantity generally amounts to from 5 to 30 % by volume, preferably from 10–20% by volume, of the total filling volume, sought after. Its ceiling corresponds to the capacity of this very filling volume. In case, however, that a pressure eruption upon the start of the continuous operation is acceptable, the aforedescribed preventive measures can be dispensed with, of course. Upon the desired filling level of autoclave 6 being attained, its contents (i.e. liquid reaction mixture and gaseous hydrogen chloride) may be transferred into further autoclaves 7, 8. As far as the derivatives of easy fluorination are concerned, such as benzotrichloride, o- or p-chloro-benzotrichloride, one single autoclave is sufficient. This transfer may be carried out automatically by means of an ascending pipe set up at the desirable height with a connecting pipe 9 to reach 7 or 8. Alternatively the contents are withdrawn from autoclave 6 through a connecting line 10 or from the last of the autoclaves of the cascade 8 through a connecting line 9 by means of said control devices V (on 9) or V (on 10) most conveniently conveyed to a fractionating column 13 operating under pressure by means of a valve 11 set up for pressure control of the autoclave, through a pipe 12. In this fractionating column 13 the hydrogen chloride previously formed is separated and removed at the top of the column through pipe 14. The liquid sump phase being double-phased by now is then removed through pipe 15 and in the separator 16 subjected to separation in known manner. The reaction product may be re-cycled for further work-up or purification through pipe 17. The separated excess hydrogen fluoride is re-cycled through pipe (18) for further reaction.

The fluctuations and whirls produced upon feeding the autoclave produce such an intense blending of the reaction mixture, so that no additional agitating or blending devices whatsoever are required.

The equipment devices or parts of same required for the execution of the reaction and for subsequent work-up of the reaction mixture may all consist of reasonably anti-corrosive materials such as iron, chromium, nickel, copper and noble metals and their alloys as well. Practice has singled out low-carbon steel as the best suitable autoclave material.

Suitable starting materials for the process according to the invention are all derivatives of benzene with one or several trichloromethyl groups, such as trichloromethylbenzene, o-bis-trichloromethyl benzene, m-bis-trichloromethylbenzene, p-bis-trichloromethylbenzene, monochloro-trichloromethylbenzene, monofluoro-trichloromethylbenzene, dichloro-trichloromethylbenzene, o-trichloromethylbenzoyl chloride, m-trichloromethylbenzoyl chloride or p-trichloromethylbenzoyl chloride.

In general, the yield rates for the reaction products fluorinated according to the invention are very high and can be practically quantitative, if the process is operated permanently. Moreover, even a continuous operation for preparing the compounds of the examples run for several weeks did not produce any discernable resinifications of the equipment or any other secondary reactions susceptible to cause trouble.

The fluorination products prepared are important intermediate products for the preparation of dyestuffs and pesticidal compositions, e.g. the pesticidal composition offered by Messrs. Ciba-Geigy under the commercial designation of "Cotoran".

The following examples illustrate the invention:

EXAMPLE 1

The reaction components being preheated in a preheaterdevice preceding a 1000 l autoclave, the latter is first charged with 200 l of liquid hydrogen fluoride and then fed at 120°C at the rate of a molar proportion of 1:4.3 with 500 kg of benzotrichloride and 220 kg of hydrofluoric acid which are pumped in per hour. The reaction pressure is mounting steadily during this operation. At the pressure of 40 atmospheres above atmospheric pressure the connection to the pressure-maintaining device being adjusted to this pressure level is opened. An ascending pipe built-in at a suitable height permit transfer through said pressure-maintaining device first of hydrogen chloride and, at a filling level of 750 ml, also of liquid reaction mixture into the distillation equipment set up subsequently, where hydrogen chloride is first eliminated by distillation under a pressure of 40 absolute atmospheres. Hydrogen fluoride being separated at 25°C to yield benzotrifluoride at a yield rate of 94 % of the theoretical yield, calculated on the benzotrichloride initially used. The crude product contains hydrogen fluoride at a rate of less than 0.5 weight percent.

EXAMPLE 2

The operation is carried out according to example 1, but subsequently to the 1000 l autoclave two more 500 l autoclaves are set up as a cascade all having the same reaction temperature. The actual reaction volume of each of these autoclaves amounts to 350 l being adjusted by the immersion depth of the connecting ascending pipes. The pressure maintenance and the evacuation are carried out in the third autoclave. Dosage and reaction correspond to what is stated in example 1. Benzotrifluoride is obtained at a yield rate of 98 % of the theoretical yield, calculated on the benzotrichloride initially used.

The crude product in the collecting receptacle contains less than 0.5 weight percent of hydrogen fluoride.

EXAMPLE 3

The first of the two 500 l autoclaves set up in cascade is charged with 125 kg of hydrofluoric acid and at 90°C are fed in by pumping 228 kg of p-chlorobenzotrichloride and 88 kg of hydrofluoric acid (molar proportion 1:4.43) per hour. At a reaction pressure of 40 atmospheres above atmospheric pressure, which is maintained at that level, the connection to the second reactor is opened. The reaction temperature is then 140°C. For the rest, the description of example 1 is followed. p-chlorobenzotrifluoride is obtained at a yield rate of 97.6 % of the theoretical yield, calculated on the p-chlorobenzotrichloride initially used. The crude product contains less than 0.5 weight percent of hydrogen fluoride.

EXAMPLE 4

The operation is carried out with the autoclave connection and under the pressure conditions as stipulated in example 3. So as to preheat the reactants to 120°C a preheater device of 90 l volume proceeds the cascade. 125 kg of hydrogen fluoride are first charged and subsequently added through this preheater-device are 100 kg of hydrogen fluoride and 233 kg of o-chloro-benzotrichloride (molar proportion 1:4.95) in doses per hour. The first autoclave has a temperature of 120°C, the next that of 100°C. o-chloro-benzotrifluoride is obtained at a yield rate of 97.9 % of the theoretical yield, calculated on the o-chloro-benzotrichloride initially used. The crude product contains hydrogen fluoride at a rate of less then 0.3 weight percent.

EXAMPLE 5

After having charged an autoclave according to example 3 under the same pressure conditions also specified in example 3 with 125 kg of hydrogen fluoride, a quantity of 84 kg of m-xylene-hexachloride and of 90 kg of hydrogen fluoride are fed in per hour (molar proportion 1:16.7). The reaction components are preheated to 125°C. The reaction temperature is 130°C in the first autoclave and 120°C in the second. m-xylenehexafluoride is obtained at a yield rate of 93.5 % of the theoretical yield, calculated on the m-xylenehexachloride initially used.

EXAMPLE 6

The setting of the equipment and the pressure conditions are those stipulated in example 3. 125 l of hydrogen fluoride are charged and preheated to 125°C. 150 kg of m-trichloromethylbenzoylchloride and — simultaneously — 100 kg of hydrofluoric acid (molar proportion 1:8.60) are fed in per hour at an autoclave temperature of 125°C. The mixture of the reactants had been preheated previously to 120°C. The temperature for both processing steps is also 125°C. m-trifluoromethylbenzoylfluoride is obtained at a yield rate of 87.3 % of the theoretical yield, calculated on the derivative of trichloromethyl initially used.

We claim:
1. In a process for the preparation of the derivative of benzene containing at least one trifluoromethyl group by reaction of the corresponding trichloromethyl compound with liquid hydrogen fluoride, by subsequently distilling the reaction products under pressure thus eliminating the newly formed hydrogen chloride, and by subsequently isolating the remaining reaction products, the improvement for continuous processing which comprises continuously feeding the reactants into a reaction zone under an effective pressure in excess of 20 absolute atmospheres to maintain a sufficiently homogeneous reaction mixture to solubilize the reactants, with the hydrogen fluoride reactant being in at least a 25 mol % excess as compared to the stoichiometric proportion, blending said mixture in said zone by means limited to the agitation caused by the pressurized feeding of the reactants into said zone, withdrawing the reaction products from said zone proportionately to the feeding-in rate of the reactants, said reaction zone being maintained in a reaction temperature range of above 80° to about 150°C, said reaction having been initiated by precharging said zone with liquid hydrogen fluoride alone or in homogeneous mixture with said trichloromethyl compounds and hydrogen chloride to a pressure of at least 20 atmospheres.

2. Process according to claim 1 wherein the reaction is carried out at a pressure of from 30 to 50 absolute atmospheres.

3. Process according to claim 1 wherein the reaction is carried out at a temperature of from 85° to 150°C.

4. Process according to claim 1 wherein the reaction is carried out at a temperature of from 90° to 130°C.

5. Process according to claim 1 wherein the stoichiometric excess rate of hydrogen fluoride is from 30 to 300 mole %.

6. Process according to claim 1 wherein the stoichiometric excess rate of hydrogen fluoride varies from 40 to 200 mole %.

7. Process according to claim 1 wherein the reaction is carried out with an average residence time of the reaction components of from 30 to 300 minutes.

8. Process according to claim 1 wherein the reaction is carried out with an average residence time of the reaction components of from 50 to 100 minutes.

9. The process according to claim 1 wherein said pre-charging of said zone is at a temperature below 80°C and with liquid hydrogen fluoride alone.

10. A process according to claim 1 wherein the reaction zone comprises a cascade of from 1 to 5 separate sub-zones.

11. A process according to claim 1 wherein the reaction zone comprises a cascade of from 1 to 3 separate sub-zones.

12. A process according to claim 1 wherein the reaction pressure ranges from about 20 atmospheres to about 50 atmospheres, the reaction temperature ranges from about 80°C to about 150°C, said stoichiometric excess rate ranges from 25 mol % to about 300 mol %, and the average residence time of the reaction components in said zone ranges from 30 minutes to 300 minutes.

13. A process according to claim 12 wherein the reaction zone comprises a cascade of from 1 to 5 separated sub-zones with each sub-zone having a proportion of length to diameter of less than 10:1.

* * * * *